United States Patent [19]

Corey, Jr.

[11] Patent Number: 5,039,430
[45] Date of Patent: Aug. 13, 1991

[54] METHOD AND APPARATUS FOR COMBINING CARDIOTOMY AND VENOUS BLOOD

[75] Inventor: Edmund R. Corey, Jr., Schwenksville, Pa.

[73] Assignee: Medtronic, Inc., Minneapolis, Minn.

[21] Appl. No.: 439,459

[22] Filed: Nov. 20, 1989

[51] Int. Cl.⁵ ............................................. B01D 19/02
[52] U.S. Cl. .................................... 210/806; 55/38; 55/178; 210/188; 210/337; 210/436; 210/437; 210/455; 210/458; 210/472; 210/485; 210/489; 210/492; 604/4
[58] Field of Search ................. 210/750, 806, 94, 188, 210/436, 437, 455, 457, 458, 483, 485, 488, 489, 492, 472, 494.1, 494.3, 493.1, 718, 337, 335; 604/4, 51, 52; 128/DIG. 3; 55/178, 38

[56] References Cited

U.S. PATENT DOCUMENTS

| | | | |
|---|---|---|---|
| 3,507,395 | 4/1970 | Bentley | 210/443 |
| 3,768,653 | 10/1973 | Brumfield | 210/188 |
| 3,891,416 | 6/1975 | Leonard et al. | 55/178 |
| 3,993,461 | 11/1976 | Leonard et al. | 55/178 |
| 4,157,965 | 6/1979 | Raible | 210/305 |
| 4,164,468 | 8/1979 | Raible | 210/436 |
| 4,208,193 | 6/1980 | Munsch et al. | 55/36 |
| 4,243,531 | 1/1981 | Crockett et al. | 210/188 |
| 4,599,093 | 7/1986 | Steg, Jr. | 210/188 |
| 4,705,497 | 11/1987 | Shitaokoshi et al. | 604/4 |
| 4,737,139 | 4/1988 | Zupkas et al. | 604/4 |
| 4,743,371 | 5/1988 | Servas et al. | 210/188 |
| 4,758,337 | 7/1988 | Kohn et al. | 210/472 |
| 4,919,802 | 4/1990 | Katsura | 210/188 |

FOREIGN PATENT DOCUMENTS

2452936 12/1980 France ............................ 210/472

Primary Examiner—W. Gary Jones
Attorney, Agent, or Firm—Reed A. Duthler

[57] ABSTRACT

A combined cardiotomy and venous return reservoir which combines defoamed and filtered cardiotomy blood with venous blood in a common chamber and then passes the combined blood fractions through a second defoaming element to achieve positive mixing of the blood fractions before they exit the device.

10 Claims, 6 Drawing Sheets

METHOD AND APPARATUS FOR COMBINING CARDIOTOMY AND VENOUS BLOOD

BACKGROUND OF THE INVENTION

Cardiotomy reservoirs which reclaim blood drawn from a surgical site by defoaming and filtering the blood to remove foreign matter are well known. References which describe various cardiotomy reservoir structures include U.S. Pat. Nos. 3,507,395; 3,768,653; 3,891,416; 3,993,461; 4,157,965; 4,164,468; 4,208,193; 4,243,531; 4,705,497; and 4,743,371.

Typically, before it is oxygenated and returned to the body, blood which has been cleansed and defoamed in a cardiotomy reservoir is combined with blood extracted from a vein in the patient's body. To simplify the necessary connections for such procedures and to reduce the volume of the extracorporeal blood circuit, it has been proposed that cardiotomy blood and venous blood be combined in a cardiotomy reservoir and the combined fractions directly fed into an oxygenator. The depth filter media used in modern cardiotomy reservoirs, however, can damage healthy cells, especially under high pressures and, therefore, blood obtained directly from a venous shunt which is uncontaminated by foreign matter should not be forced through such filter media if possible.

Combined cardiotomy and venous return reservoirs which provides separate flow paths into common collection reservoirs for venous return blood obtained and for cardiotomy blood are described in U.S. Pat. Nos. 4,705,497 and 4,737,139.

U.S. Pat. No. 4,705,497 describes a combined cardiotomy and venous return reservoir in which the venous blood does not pass through any filtering or defoaming element and in which the venous and cardiotomy blood separately enter a pooling reservoir at different levels. The device includes no means to assure positive mixing of the blood fractions. The device of U.S. Pat. No. 4,737,139 has a significant disadvantage in that the blood from the two sources is never positively mixed. In this device the cardiotomy blood is filtered through reticulated polyurethane foam defoaming element, a felt depth filter and a mesh fabric screen while the venous blood is only passed through the polyurethane foam and mesh fabric elements. The device is arranged in such a manner that the venous and cardiotomy blood fractions have separate flow paths into the common reservoir with the venous blood entering the common collection reservoir below the cardiotomy blood. This flow pattern can result in significant layering of the blood, especially since the exit port is at the bottom of the collection reservoir and the venous blood typically is fed into the device at a much higher rate than cardiotomy blood.

SUMMARY OF THE INVENTION

In one aspect the present invention pertains to an improved combined venous return and cardiotomy reservoir in which blood from both sources is positively mixed before entering the collection reservoir so as to avoid the layering problems previously experienced with devices of the type described in U.S. Pat. No. 4,737,139.

Another aspect of the invention comprises a method for collecting and treating blood from venous and surgical site sources during a surgical procedure which includes the steps of passing blood from said surgical site source through a first defoaming element and a depth filter element to produce a filtered surgical site blood fraction; combining said filtered surgical site blood fraction with said venous source blood to produce a combined blood fraction; and then mixing the combined blood fraction by passing it through a second defoaming element.

Yet a further aspect of the invention comprises a novel structure for a combined cardiotomy and venous return reservoir in which a combined chamber for cardiotomy and venous blood is nested within an intermediate blood fraction mixing chamber which is, in turn, nested within an outer collection and return reservoir.

An still further aspect of the invention comprises an improved structure for a blood defoaming device which provides an unhindered vertically extending space between two defoaming elements to allow separated air bubbles to rise to the blood surface more efficiently. This aspect of the invention has advantages both in the combined cardiotomy venous/return reservoir described above and in a simpler venous return reservoir embodiment.

DETAILED DESCRIPTION OF THE PREFERRED EMBODIMENT

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

The preferred combined cardiotomy and venous return reservoir is generally designated in the figures by the numeral 10. The numeral 12 generally designates a blood heater/oxygenator device, above which device 10 may be detachably mounted to form a unitary column structure. Device 12 is not part of the invention herein.

Device 10 comprises a cover member 14 which includes at least one cardiotomy port 16 providing inlet means into the interior of the device 10. Suitably cover 14 also includes optional luer ports 18 by means of which medicines or other blood treatments may be optionally introduced into the device, a quick prime port 20 for priming the interior of device 10, and a vent port 22 for releasing air separated from the blood within the device.

Figure 1:
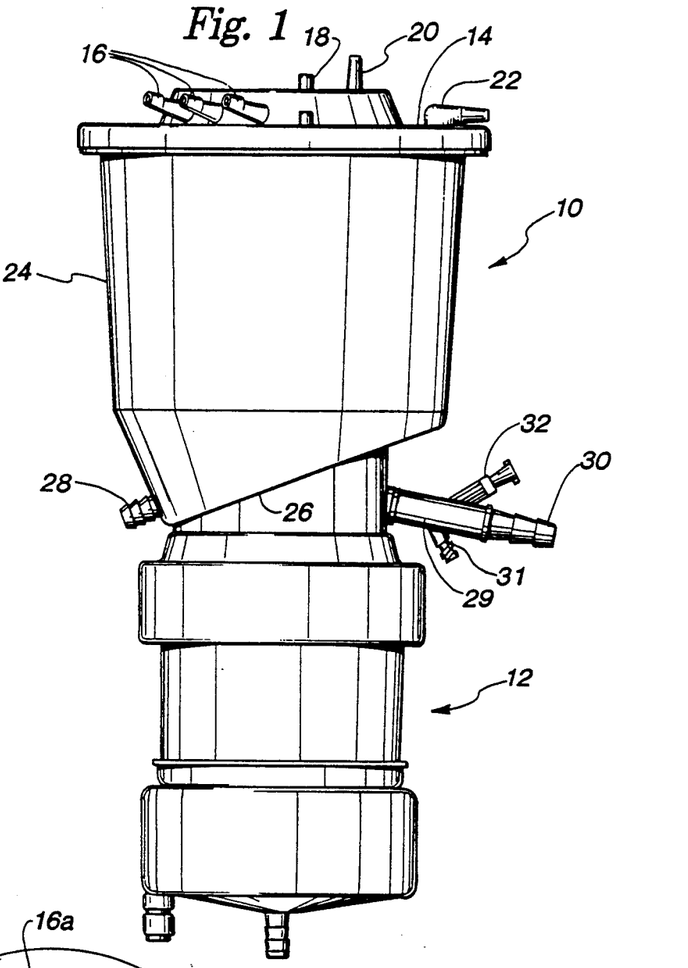
FIG. 1 is a side elevational view of the preferred form of the subject invention mounted above an associated blood oxygenating device. In this figure the blood inlet port structure has been rotated 90° from its normal position for purposes of illustration.
Figure 2:
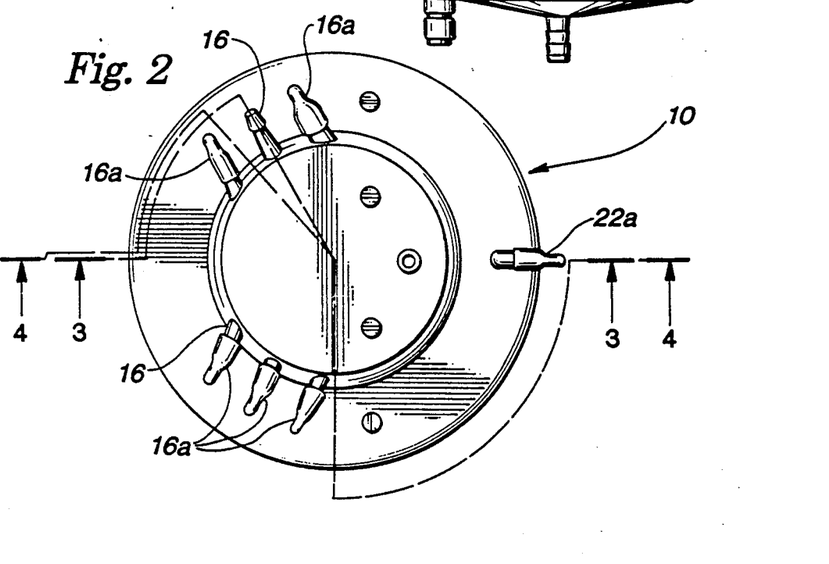
FIG. 2 is a top plan view of the preferred form of the device of the invention.

The housing of device 10 further comprises a generally cylindrical sidewall 24 and a bottom 26 which are desirably formed as an integral unit. Desirably the sidewall 24 is tapered inwardly, particularly near the bottom and the bottom 26 is tapered downwardly toward one side, as shown in FIG. 1. By this construction the blood is caused to naturally drain towards the exit port 28 which is likewise desirably disposed at a downward angle to facilitate drainage.

Device 10 is also provided with a venous blood inlet structure 29 which provides means for introducing venous blood into the interior of device 10. In FIG. 1 this structure has been rotated 90° from its normal position for purposes of illustration. Inlet structure 29 includes the blood inlet port 30 and optional side port 31 by means of which medicines or other blood treatments may be introduced. Desirably inlet structure 29 also includes a temperature measuring receptacle port 32 for receiving a temperature measuring probe.

Suitably the respective ports 16, 18, 20, 22, 28, 30 and 31 are provided with removable caps to maintain sterility prior to use and to seal unused ports during operation of the device. In the figures the numerals 16a, 18a, 20a, 22a, 28a, 30a, and 31a refer to the respective port caps.

The interior structure of device 10 is shown in FIGS. 3-7. Cardiotomy blood entering port 16 is passed through a first annular defoaming element 34. Suitably element 34 comprises a open cell, blood compatible, synthetic polymer foam material which collapses bloodfoam as the blood passes therethrough. Defoaming element 34 is preferably formed of a thermally reticulated polyurethane foam having, for example, a 20-pore per inch size. Preferably element 34 is treated with a medical antifoam agent to assist the defoaming step. Suitable antifoam agents include silicone antifoam agents such as Antifoam A available from Dow Chemical Company.

Figure 3:
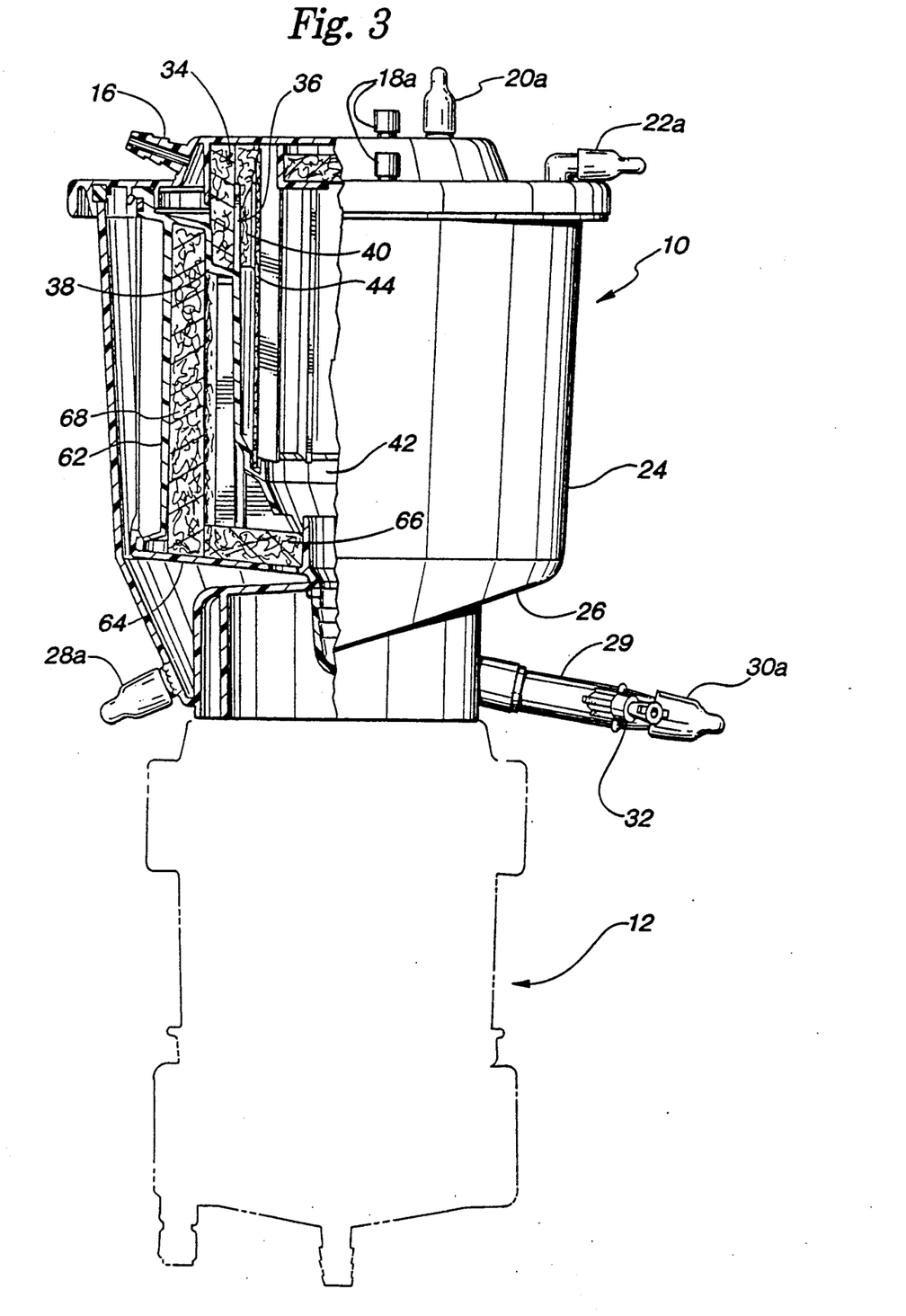
FIG. 3 is a sectional elevational view taken along line 3—3 of FIG. 2.
Figure 4:
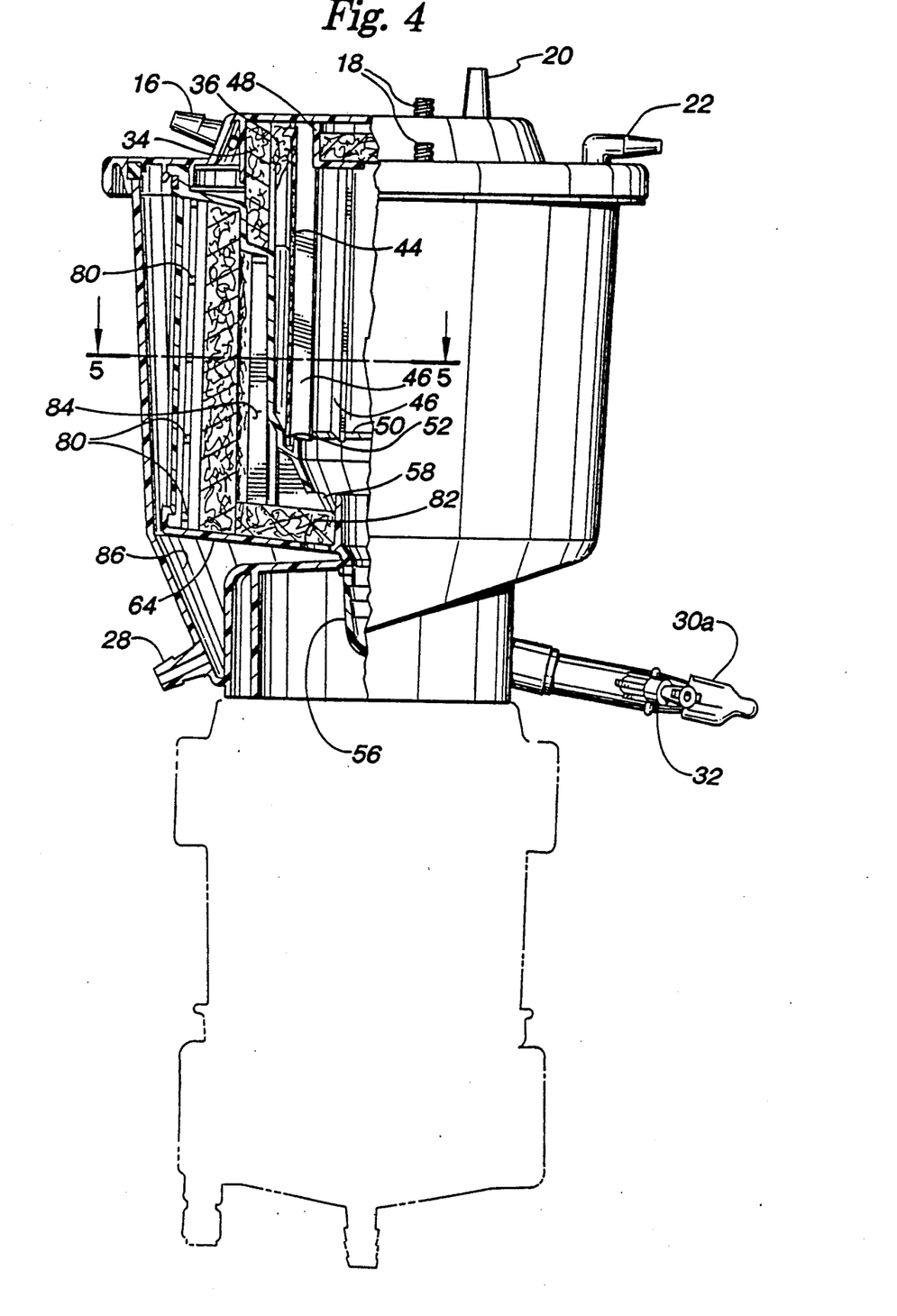
FIG. 4 is a sectional elevational view taken along line 4—4 of FIG. 2, with some port caps removed.

The defoaming element 34 is supported by a plurality of prongs 36 extending upwardly from internal wall member 38. The prongs 36 allow blood to pass therearound and into a void space 40 from which the cardiotomy blood passes into a central blood-combining chamber 42 through tubular depth filter element 44. Depth filter element 44 is held in place by a plurality of rigid plastic fin members 46 so that blood can flow through the depth filter between the fins. Fins 46 are in turn held in place by integral annular rings 48 and 50 at the upper and lower ends of fins 46, respectively. The base of the depth filter element 44 is fitted into a groove within an annular gasket 52 to prevent cardiotomy blood from flowing into the combining chamber 42 without passing through the depth filter element 44. The depth filter element 44 suitably comprises a nonwoven felt of a synthetic material such as polypropylene or polyester and provide a system of complex pathways for filtering particulate matter in the blood. A suitable depth filter material is a fibrous polyester felt having a mean pore diameter of 20 microns, which may optionally be pretreated with a wetting agent.

While the cardiotomy blood must first pass through defoaming element 34 and depth filter element 44 in order to enter the combining chamber 42, venous blood entering device 10 is passed directly into the combining chamber via a conduit 56 which extends through the bottom of the device. Conduit 56 is free of depth filter material and is desirably likewise unobstructed by any defoaming material.

The venous blood and cardiotomy blood fraction are combined within chamber 42 and then exit therefrom via a plurality of holes 58 which ring the bottom of chamber 42. Holes 58 open into an intermediate mixing chamber 60 defined by wall 38 and an outer mesh fabric element 70 which is supported by rigid side supporting wall member 62 and rigid bottom supporting wall member 64. Inside the rigid supporting wall members 62 and 64, circular defoaming element 66 and cylindrical defoaming element 68 are located. Suitably elements 66 and 68 comprise the same material as defoaming element 34 although it is not necessary to treat element 68 with a defoaming agent.

Figures 5, 5A:
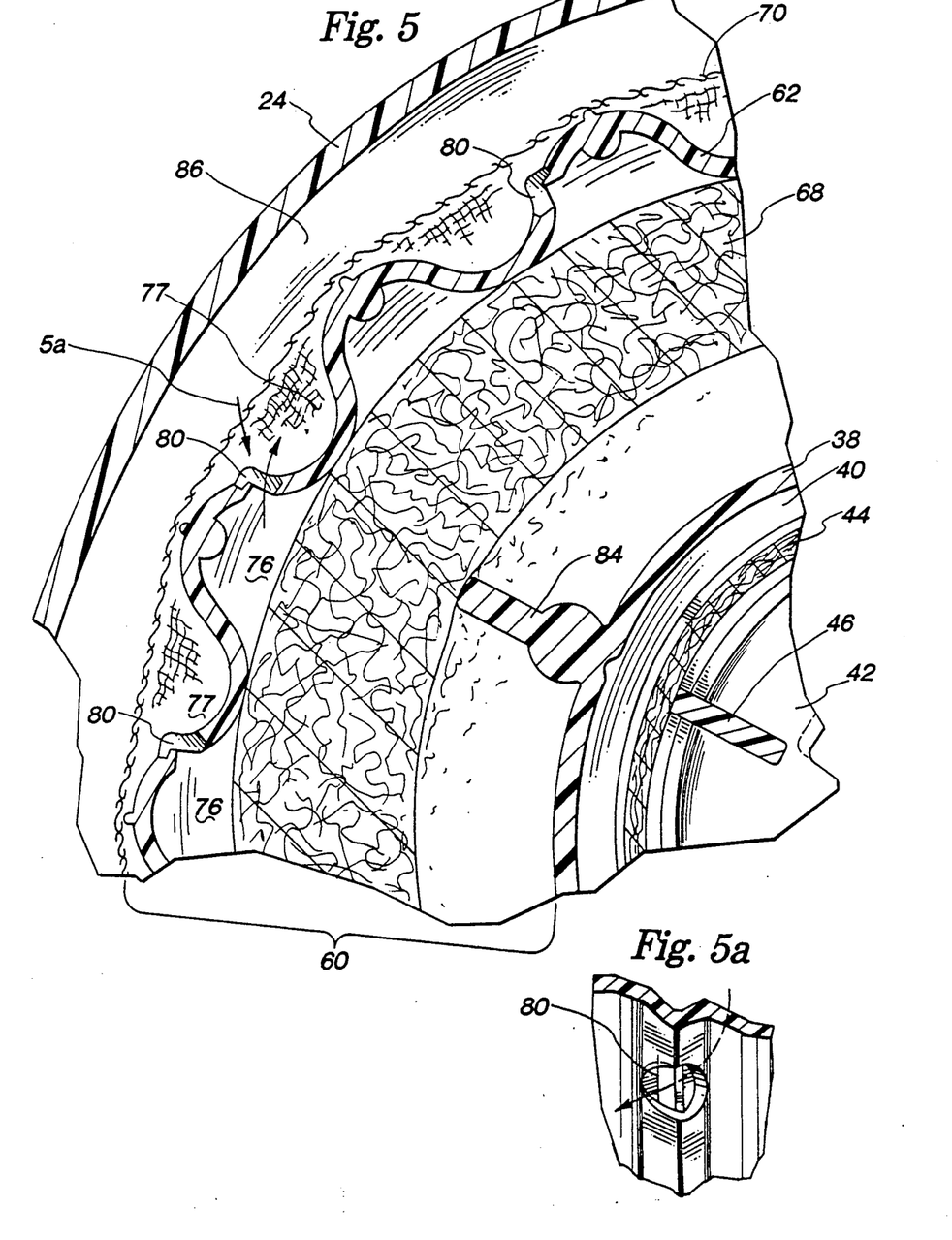
FIG. 5 is an enlarged sectional fragment taken at line 5—5 of FIG. 4.
FIG. 5a is a fragmentary pictorial view taken at arrow 5a of FIG. 5.

Supporting sidewall 62 has a scalloped shape as best shown in FIG. 5. Suitably wall 62 is integrally formed with internal wall 38, the two walls meeting at a joint 76 at the top thereof which snaps into a mating structure in top 14 of device 10. The top of fabric mesh 70 is folded over and stitched to form a hem into which is inserted a tie-strap 72. Tie-strap 72 fits into a groove 74 within the joint member 76 so as to securely hold the sock in place. Suitably tie-strap 72 comprises two or more plastic cable ties linked in series.

Referring again to FIG. 5, it can be seen that the scalloped shape of wall member 62 is provided with a series of spaces 76 within chamber 60 between the defoaming element 68 and supporting wall 62 and a complementary series of spaces 77 between the outside of supporting wall 62 and filter 70.

Spaced around the circumference of wall 62 at several levels are a plurality of openings 80 through which blood may flow as shown by the directional areas in FIGS. 5 and 5a. Suitably the bottom wall 64 of chamber 60 is also provided with a plurality of openings 82 which ring conduit 56.

Within chamber 60 there are also provided a series of vertical rigid fin members 84 which extend outwardly from wall 38 to locate and support the annular defoaming element 68. As can best be seen in FIG. 4, fins 84 also extend downwardly to depress the defoaming element 66, thereby holding it in place as well.

Outside of the mesh fabric element 70 is a return collection chamber 86 defined by the space between the outer walls of device 10 and mesh fabric element 70. Mesh fabric element 70 further filters and defoams the combined blood fractions. Suitably it is a woven nylon or polyester screen.

In operation, the combined blood entering the intermediate mixing chamber 60 via holes 58 passes through defoaming element 66 or 68, holes 82 or 80 and then through the mesh fabric element 70, thereby assuring that the combined cardiotomy blood and venous blood is positively and thoroughly mixed by the time it enters the collection chamber 86. In this manner, the layering of blood from the different sources which can occur in devices such as described in U.S. Pat. No. 4,737,139 is avoided.

Figure 6:
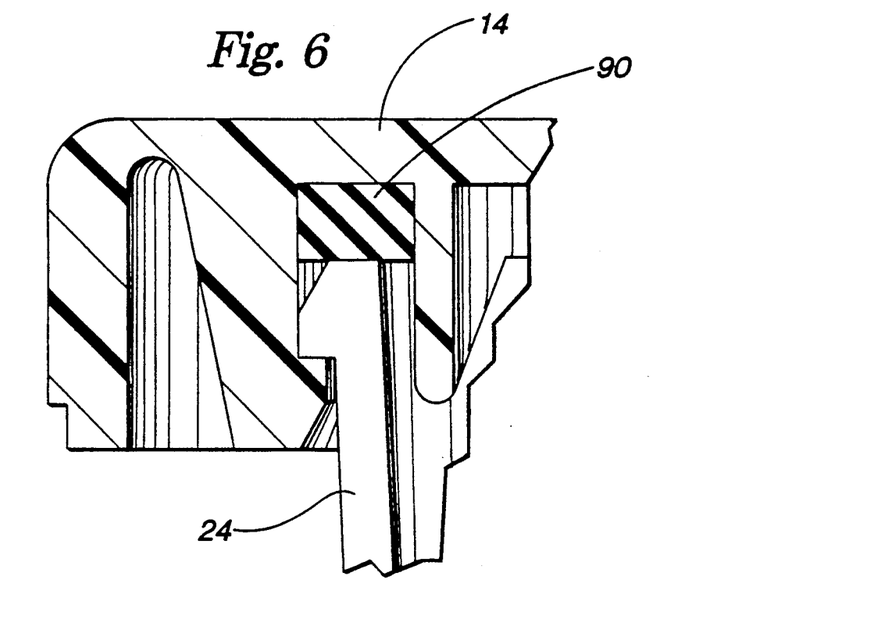
FIG. 6 is a greatly enlarged fragmentary detail view of part of FIG. 3 showing the joint between the top and sidewalls of the device.

Referring to FIG. 6, it can be seen that a gas-tight and liquid-tight seal is achieved between the cover 14 and the sidewall 24 by means of a flexible gasket member 90.

Figure 7:
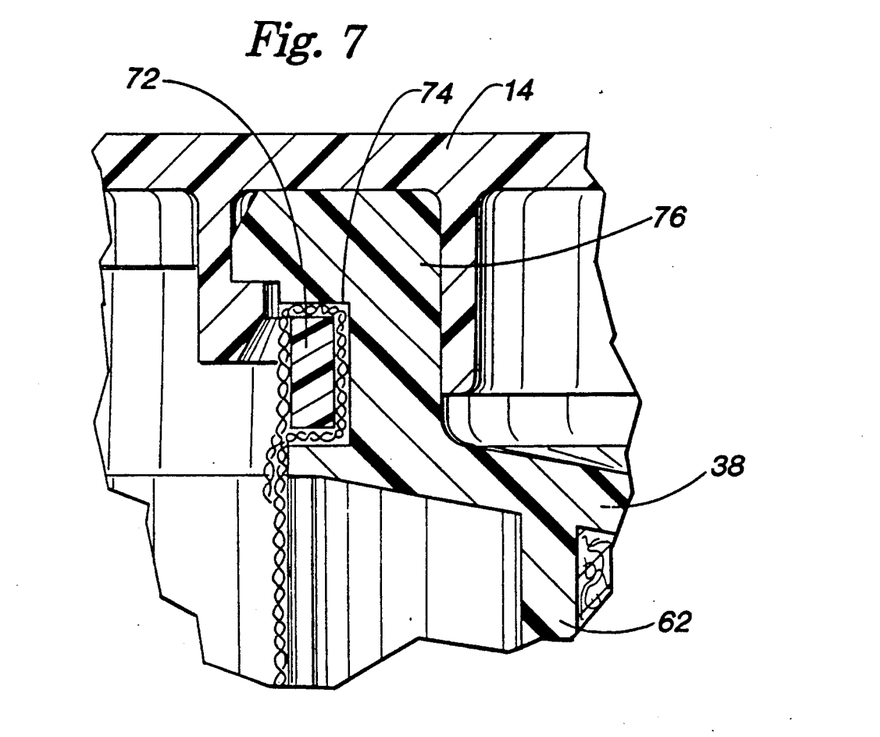
FIG. 7 is a greatly enlarged fragmentary detail view of part of FIG. 3 showing the joint between the top of the device and the internal wall structure.

No such gasket is provided in the snap joint between internal wall joint 76 and cover 14, as shown in FIG. 7. The absence of a gasket between joint 76 and cover 14 assures that the air pressure between the inner and outer chambers of the device is equilibrated to prevent pressure buildup within the device which would prevent the defoaming operation and the proper venting of gas bubbles separated from the blood.

A particular feature of the inventive structure are the spaces 76 and 77 which are interposed between the defoaming element 68 and the mesh fabric element 70. Gas bubbles separated from the blood will rapidly and efficiently rise to t he surface within these spaces to provide more efficient defoaming action when blood is moving through the device at high volumes.

Figures 8, 9, 10:
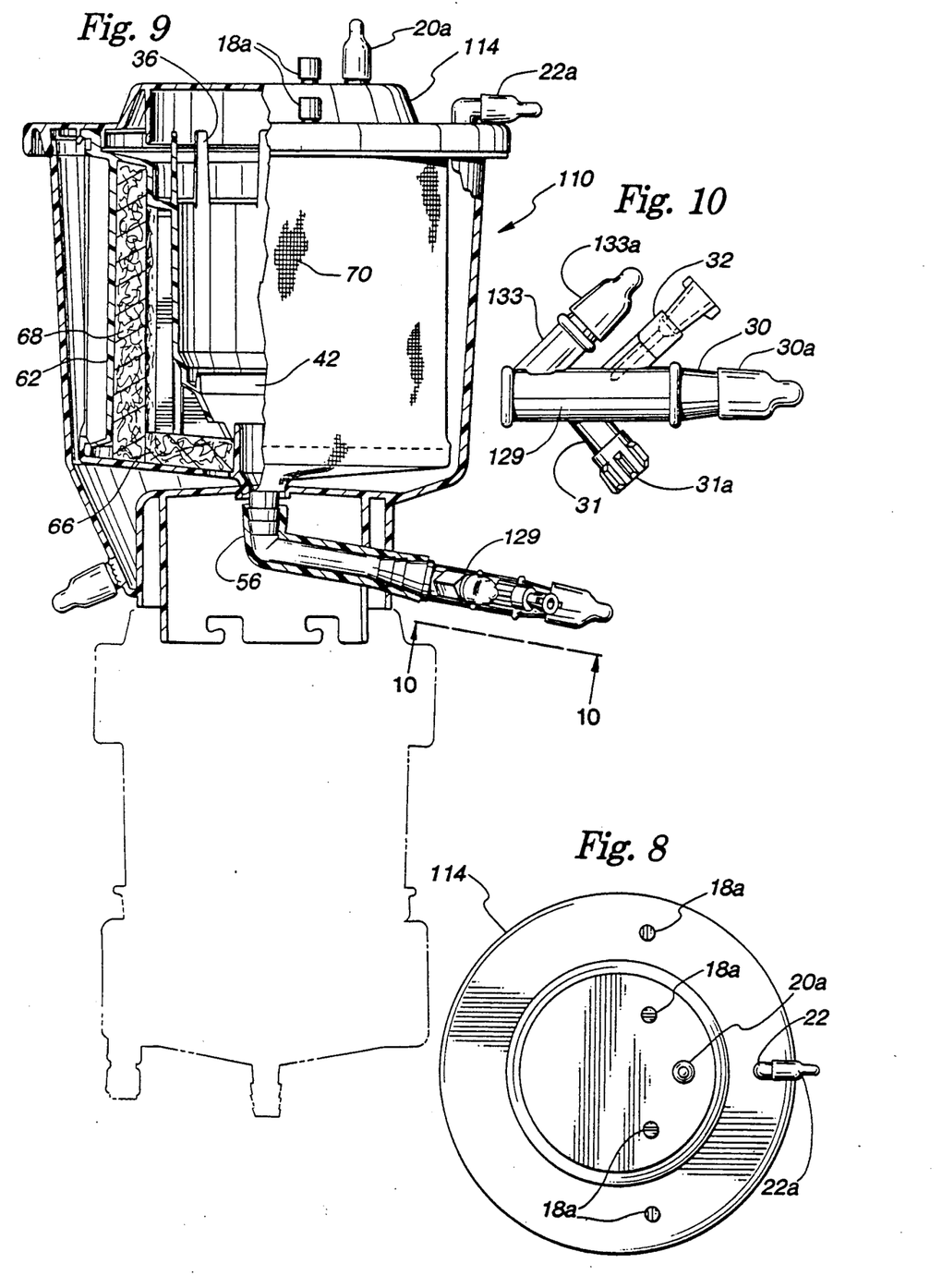
FIG. 8 is a top plan view of an alternative device employing some of the features of the invention.
FIG. 9 is a side elevational view of the device of FIG. 8 with parts cut away.
FIG. 10 is a bottom view taken along line 10—10 of FIG. 9.

FIGS. 8-10 illustrate a simple venous return reservoir generally designated by the numeral 110 which also utilizes this aspect of the invention. The return reservoir 110 has a cover member 114 which is similar to cover 14 except that no cardiotomy ports are provided. The internal structure of the device is identical to that of device 10 except that defoaming element 34 and deep filtering element 44, together with its removable supporting structure, have been omitted. Other structures within device 110 which are identical to those of device 10 are identified by the same numerals.

Although the device 110 does not combine blood fractions within the chamber 42, scalloped wall member 62 provides device 110 with the same advantage of an efficient gas separation which it provides in device 10.

The inlet port structure 129 of device 110 includes inlet port 30, side port 31 and temperature receptacle port 32 and, in addition, a second inlet port 133 for providing optional access to a separate cardiotomy reservoir. Port 133 is sealed with a cap member 133a when not in use.

In both devices 10 and 110, the rigid elements (cover, exterior side and bottom walls and the interior rigid wall members) are suitably manufactured of a biocompatible plastic such as polycarbonate, acrylic or polyurethane plastics. Lexan 4517 or Merlon ™ M39RF-1112 polycarbonate sold by General Electric Co. and Mobay Chemical Corp., respectively, are suitable materials for such parts.

This completes the description of the preferred and alternate embodiments of the invention. Those skilled in the art may recognize other equivalents to the specific embodiment described herein which equivalents are intended to be encompassed by the claims attached hereto.

What is claimed is:

1. A device for treatment and collection of blood from two different sources during a surgical procedure comprising:
    a hollow housing;
    a combining chamber within a portion of the housing for collecting and combining blood from said two sources;
    first inlet means defining a flow path for introducing blood from said first source into the combining chamber, said first inlet means including an inlet port into the housing, a first defoaming element between the inlet port and the combining chamber, and a depth filter media between the first defoaming element and the combining chamber;
    second inlet means defining a flow path for introducing blood from the second source into the combining chamber without passing through a depth filter media, said second inlet means including a second inlet port into the housing;
    a return chamber located in the second portion of the housing;
    outlet means including an outlet port through the housing defining a blood flow path from said return chamber to the exterior of the housing;
    an intermediate mixing chamber between said combining chamber and said return chamber;
    second defoaming means located within said mixing chamber; and
    conduit means providing a blood flow path from said combining chamber through said second defoaming means and into the return chamber.

2. A device as in claim 1 wherein said housing has a generally cylindrical structure, said combining chamber is located centrally within the device and is rested within said intermediate chamber, and wherein said intermediate chamber is nested within said return chamber.

3. A device as in claim 2 wherein said intermediate chamber includes a rigid porous vertically extending support wall member having a scalloped circumference and providing support for a mesh fabric surrounding said porous support wall member.

4. A device as in claim 3 wherein the second defoaming means comprises an annular foam element within said rigid porous wall member, and the scalloped circumference of said porous wall member defines a plurality of vertically extending spaces between said wall and the foam element on one side and between the wall and the mesh fabric element on the other side.

5. A device as in claim 2 wherein second defoaming means comprises an annular foam element within said mixing chamber.

6. A method for collecting and treating blood from venous and surgical site sources during a surgical procedure comprising:
    passing blood from said surgical site source through a first defoaming element and a depth filter element to produce a filtered surgical site blood fraction,
    combining said filtered surgical site blood fraction with generally unfiltered venous source blood to produce a combined blood fraction, and then
    mixing the combined blood fraction by passing it through a second defoaming element.

7. A method as in claim 6 wherein said second defoaming element comprises an open pore foam material.

8. In a blood reservoir device including defoaming means comprising an open pore foam material surrounded by a mesh fabric material, the improvement comprising a rigid porous spacer element between said foam material and said mesh fabric, the spacer element constructed to define a plurality of vertically extending spaces between said fabric and said spacer on one side and between said spacer and said foam material on the other side.

9. A blood reservoir as in claim 8 wherein said foam element and said fabric elements have a generally cylindrical shape and said porous spacer comprises a porous vertically extending wall therebetween, said wall having a scalloped circumference.

10. A device for treating and collecting blood fractions from two different sources during a surgical procedure comprising:
    a hollow housing;

first and second introduction means for introducing blood fractions from respective first and second sources;

a first defoaming means for defoaming blood from said first source, as it passes therethrough;

a depth filtering element for deep filtering blood from said first source after it has been defoamed;

a combining means for combining the defoamed and deep filtered blood fraction from said first source and substantially unfiltered blood fraction from said second source;

second defoaming means for defoaming the combined blood fractions as they pass therethrough; and exit means for removing the combined blood from the device after it has passed through the second defoaming means.

* * * * *